(12) United States Patent
West, Jr.

(10) Patent No.: US 8,361,065 B2
(45) Date of Patent: *Jan. 29, 2013

(54) ELECTROSURGICAL INSTRUMENT WITH AN ABLATION MODE AND A COAGULATION MODE

(75) Inventor: Hugh S. West, Jr., Sandy, UT (US)

(73) Assignee: HS West Investements, LLC, Sandy, UT (US)

( * ) Notice: Subject to any disclaimer, the term of this patent is extended or adjusted under 35 U.S.C. 154(b) by 913 days.

This patent is subject to a terminal disclaimer.

(21) Appl. No.: 12/171,150

(22) Filed: Jul. 10, 2008

(65) Prior Publication Data

US 2010/0010485 A1    Jan. 14, 2010

(51) Int. Cl.
*A61B 18/14* (2006.01)
(52) U.S. Cl. .......................................... 606/37; 606/41
(58) Field of Classification Search .................. 606/37, 606/39, 40, 42; 600/393; 607/148
See application file for complete search history.

(56) References Cited

U.S. PATENT DOCUMENTS

| | | | |
|---|---|---|---|
| 4,532,924 A | 8/1985 | Auth et al. | |
| 4,998,933 A | 3/1991 | Eggers et al. | |
| 5,178,620 A | 1/1993 | Eggers et al. | |
| 5,364,395 A | 11/1994 | West, Jr. | |
| 5,366,443 A | 11/1994 | Eggers et al. | |
| 5,419,767 A | 5/1995 | Eggers et al. | |
| 5,662,680 A | 9/1997 | Desai | |
| 5,860,920 A | 1/1999 | McGee et al. | |
| 5,904,681 A | 5/1999 | West, Jr. | |
| 6,024,733 A | 2/2000 | Eggers et al. | |
| 6,064,905 A | 5/2000 | Webster, Jr. et al. | |
| 6,113,595 A | 9/2000 | Muntermann | |
| 6,117,131 A | 9/2000 | Taylor | |
| 6,168,593 B1 | 1/2001 | Sharkey et al. | |
| 6,238,391 B1 | 5/2001 | Olsen et al. | |
| 6,241,724 B1 | 6/2001 | Fleischman et al. | |
| 6,254,600 B1 | 7/2001 | Willink et al. | |
| 6,264,650 B1 | 7/2001 | Hovda et al. | |
| 6,379,350 B1 | 4/2002 | Sharkey et al. | |
| 6,494,881 B1 * | 12/2002 | Bales et al. | 606/45 |
| 6,546,270 B1 | 4/2003 | Goldin et al. | |
| 6,565,561 B1 | 5/2003 | Goble et al. | |

(Continued)

FOREIGN PATENT DOCUMENTS

JP    2007044281    2/2007

OTHER PUBLICATIONS

MedWaves, Inc. Announces Receipt of United States Food and Drug Administration 510K http://www.reuters.com/article/pressRelease/idUS238383+31-Jan-2008+PRN20080131.

(Continued)

*Primary Examiner* — Michael Peffley
*Assistant Examiner* — Thomas Giuliani
(74) *Attorney, Agent, or Firm* — Workman Nydegger

(57) ABSTRACT

The electrosurgical instrument is configured to selectively perform ablation or coagulation as desired. The electrosurgical instrument includes at least two electrodes on the electrode probe that can be activated using an RF generator. The electrosurgical instrument is selectively switchable between an ablation mode and a coagulation mode by changing the amount of active surface area. In particular, in the ablation mode, a relatively small surface area is active. Thus, for a given power input, the current density is relatively high. In the coagulation mode, the active surface area is increased, thereby reducing the current density in the coagulation mode for the given power input.

28 Claims, 5 Drawing Sheets

U.S. PATENT DOCUMENTS

| | | |
|---|---|---|
| 6,592,580 B1 | 7/2003 | Stockert |
| 6,632,193 B1 | 10/2003 | Davidson et al. |
| 6,813,520 B2 | 11/2004 | Truckai et al. |
| 6,991,631 B2 | 1/2006 | Woloszko et al. |
| 7,150,746 B2 | 12/2006 | DeCesare et al. |
| 7,244,256 B2 | 7/2007 | DeCesare et al. |
| 7,537,595 B2 | 5/2009 | McClurken |
| 7,563,261 B2* | 7/2009 | Carmel et al. .................. 606/41 |
| 2002/0049438 A1* | 4/2002 | Sharkey et al. ................ 606/41 |
| 2005/0124915 A1* | 6/2005 | Eggers et al. ................ 600/568 |
| 2007/0179495 A1 | 8/2007 | Mitchell et al. |
| 2008/0077128 A1 | 3/2008 | Woloszko et al. |
| 2008/0140074 A1 | 6/2008 | Horne et al. |
| 2008/0167645 A1* | 7/2008 | Woloszko ....................... 606/40 |
| 2008/0234673 A1* | 9/2008 | Marion et al. .................. 606/45 |
| 2010/0010485 A1 | 1/2010 | West |
| 2010/0106153 A1* | 4/2010 | West, Jr. ........................ 606/33 |

OTHER PUBLICATIONS

U.S. Appl. No. 12/651,892, filed Jan. 4, 2010, Office Action dated Jun. 23, 2011.

ConMed Linvatec—Anthroscopy—Electrodes—Apr. 15, 2008 http://www.conmed.com/products_smjoint_electrodes.php.

* cited by examiner

ELECTROSURGICAL INSTRUMENT WITH AN ABLATION MODE AND A COAGULATION MODE

BACKGROUND OF THE INVENTION

1. The Field of the Invention

The present invention relates to electrosurgical instruments for alternatively ablating and coagulating tissue in an arthroscopic procedure.

2. The Relevant Technology

Electrosurgical procedures utilize an electrosurgical generator to supply radio frequency (RF) electrical power to an active electrode for cutting and/or coagulating tissue. An electrosurgical probe is generally composed of a metallic conductor surrounded by a dielectric insulator such as plastic, ceramic, or glass. The surface of the electrode remains exposed and provides the cutting or ablating surface. During an electrosurgical procedure, the metal electrode is often immersed in a conducting fluid and is brought in contact with or in close proximity to the tissue structure to be ablated or coagulated. During a procedure, the probe is typically energized at a voltage of few hundred to a few thousand volts and at a frequency between 100 kHz to over 4 MHz. The voltage induces a current in the conductive liquid and causes heating. The most intense heating occurring in the region very close to the electrode where the current density is highest.

Depending on how the electrosurgical instrument is configured, the heat generated from the device can be used to coagulate tissue (e.g., cauterize tissue) or alternatively to ablate tissue (i.e., cut tissue). To cause ablation (i.e., cutting), the electrode generates enough heat to form gas bubbles around the electrode. The gas bubbles have a much higher resistance than tissue or saline, which causes the voltage across the electrode to increase. Given sufficient power, the electrode discharges (i.e., arcs). The high voltage current travels through the gas bubbles and creates a plasma discharge. Moving the electrode close to tissue causes the plasma layer to come within a distance sufficiently close to remove or ablate the tissue.

Electrosurgical instruments can also be used for coagulating tissue. In coagulation, the current density at the electrode is configured to cause heating without cutting. The current density is kept sufficiently high to cause proteins and/or other components of the tissue to agglomerate, thereby causing coagulation. However, during coagulation, the electrode's current density is limited to prevent ablation.

Some existing electrosurgical instruments can perform both ablation and coagulation. In most cases, the physician switches between the ablation mode and the coagulation mode by reducing the power from the RF generator. Reducing the power output of the RF generator reduces the current density at the electrode, which prevents the electrode from arcing and generating a plasma. Consequently, the electrosurgical instrument will cause coagulation. Once the physician has completed the desired coagulation, the power of the RF generator can be increased to return to the ablation mode.

BRIEF SUMMARY OF THE INVENTION

The present invention is directed to an electrosurgical instrument that can selectively perform ablation or coagulation. The electrosurgical instrument includes at least two electrodes on the electrode probe that can be activated using an RF generator. The electrosurgical instrument is switchable between an ablation mode and a coagulation mode by changing the amount of active surface area. In particular, in the ablation mode, a relatively small surface area is active. Thus, for a given amount of power, the current density is relatively high. In the coagulation mode, the active surface area is increased, thereby reducing the current density in the coagulation mode for a given amount of power. In the coagulation mode, the surface area can be sufficiently large and the current density sufficiently low that the device will coagulate instead of ablate while utilizing nearly all the power available in the ablation mode. By using a large percentage of the available power, the electrosurgical instrument of the invention exhibits relatively good ablation and coagulation using the same power source and probe.

The device of the present invention can be used effectively in the ablation mode and the coagulation mode because the active surface area changes when the user switches between the coagulation mode and the ablation mode. This configuration is in contrast to existing devices where switching between a coagulation mode and an ablation mode is accomplished solely by reducing power. In such devices, the coagulation mode is operated under suboptimal conditions because a significant portion of the available power cannot be used in coagulation mode (i.e., increasing the power causes ablation, not increased coagulation). In contrast, with the device of the present invention, a relatively high power can be maintained when switching from the ablation mode to the coagulation mode because the active surface area increases. Thus, a comparatively larger amount of heat can be generated in the coagulation mode compared to the ablation mode using the same probe and the same RF generator. While not required, the device of the present invention can even be configured to allow an increase in power when switching from ablation mode to the coagulation mode, which is contrary to conventional thinking and practice.

In one embodiment of the invention, the electrosurgical instrument includes an elongate probe having a proximal end portion and a distal end portion. A first electrode is positioned on the distal end portion of the elongate probe, the first electrode is sized and configured to ablate tissue in an ablation mode of the electrosurgical instrument at a given power input. A coagulation electrode is also positioned on the distal end portion but is electrically isolated from the first electrode. The coagulation electrode is sized and configured to coagulate tissue, either alone or in combination with the first electrode, in a coagulation mode of the electrosurgical instrument at relatively high power input (e.g., the same as when the first electrode only is activated to cause ablation).

The electrosurgical instrument also includes a user operable input component, such as but not limited to a switch, that is electrically coupled to the first electrode and coagulation electrode. The user operable input component provides user selectable switching between the ablation mode and the coagulation mode. In the ablation mode the input component delivers power to the first electrode, and in the coagulation mode the input component delivers power to at least the coagulation electrode. In the coagulation mode the surface area that receives power is substantially greater than the surface that receives power in the coagulation mode. Therefore, for a given amount of power input, the device is configured to have a lower current density in the coagulation mode compared to the ablation mode.

In a preferred embodiment, the increased active surface area in the coagulation mode is provided by the device being configured to simultaneously deliver power to both the first electrode and the coagulation electrode in the coagulation mode. In this configuration, the first electrode is sized and configured to be an ablation electrode when used alone at a given power input. In the coagulation mode, the coagulation electrode is also active, thereby drawing away power to itself and thereby reducing the net effective power received by the first electrode while utilizing most, all, or even more power drive than what is required to the first electrode in the ablation mode. The first electrode and the coagulation electrode together provide an active surface area that causes coagulation of tissue using a much larger percentage of the power that could be used with just the first electrode in a coagulation mode. Simultaneous use of the first electrode and the coagulation electrode in the coagulation mode can be highly advantageous for achieving a compact probe that can be used in surgical procedures with tight size constraints.

Using relatively high power in the coagulation mode improves the efficiency and performance of the electrosurgical instrument in the coagulation mode. Nevertheless, the use of high power in the coagulation mode of dual mode electrosurgical instruments is contrary to the rationale used to operate many existing dual mode electrosurgical instruments, which reduce power to achieve coagulation and prevent ablation.

In an alternative embodiment, the first electrode can be inactivated in the coagulation mode. In this embodiment, the increased active surface area in the coagulation mode compared to the ablation mode can be provided by a coagulation electrode sized to provide the desired current density. This configuration also provides the benefits described above of using relatively high power in the coagulation mode. In addition, this embodiment can be advantageous where design restraints prevent optimal simultaneous use of the first electrode and the coagulation electrode in the coagulation mode.

The present invention also includes methods for operating an electrosurgical instrument. The method includes (i) providing an electrosurgical instrument including an elongate probe having a proximal end portion and a distal end portion, the distal end portion including a first electrode and a coagulation electrode; the electrosurgical instrument further including a user operable input component (e.g., a switch) for allowing a user to select between an coagulation mode and an ablation mode of the electrosurgical instrument; (ii) coupling the electrosurgical instrument to an RF generator that provides power to the electrosurgical instrument; (iii) selecting the ablation mode for the electrosurgical instrument using the input component and operating the electrosurgical instrument in the ablation mode; in the ablation mode, sufficient power is delivered to the first electrode to cause ablation of a patient's tissue; and (iv) selecting the coagulation mode for the electrosurgical instrument using the input component and operating the electrosurgical instrument in the coagulation mode; in the coagulation mode, sufficient power is delivered to the coagulation electrode (and optionally the first electrode) to cause coagulation of the tissue of the patient and, in the coagulation mode, a larger amount of electrode surface area is activated compared to the ablation mode. In a preferred embodiment, the method is carried out with an RF generator with a power output in a range from about 150 W to about 600 W, more preferably about 200 W to about 400 W.

These and other advantages and features of the present invention will become more fully apparent from the following description and appended claims.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF EXEMPLARY EMBODIMENTS

The present invention is directed to an electrosurgical instrument that can be selectively operated to alternatively perform ablation or coagulation. The electrosurgical instrument includes at least two electrodes on the electrode probe that can be activated using an RF generator. The electrosurgical instrument is switchable between an ablation mode and a coagulation mode by changing the effective active surface area. In particular, in the ablation mode, a relatively small surface area is active. Thus, for a given power input, the current density is relatively high. In the coagulation mode, the active surface area is increased, thereby reducing the current density in the coagulation mode for the given power input.

Figure 1:
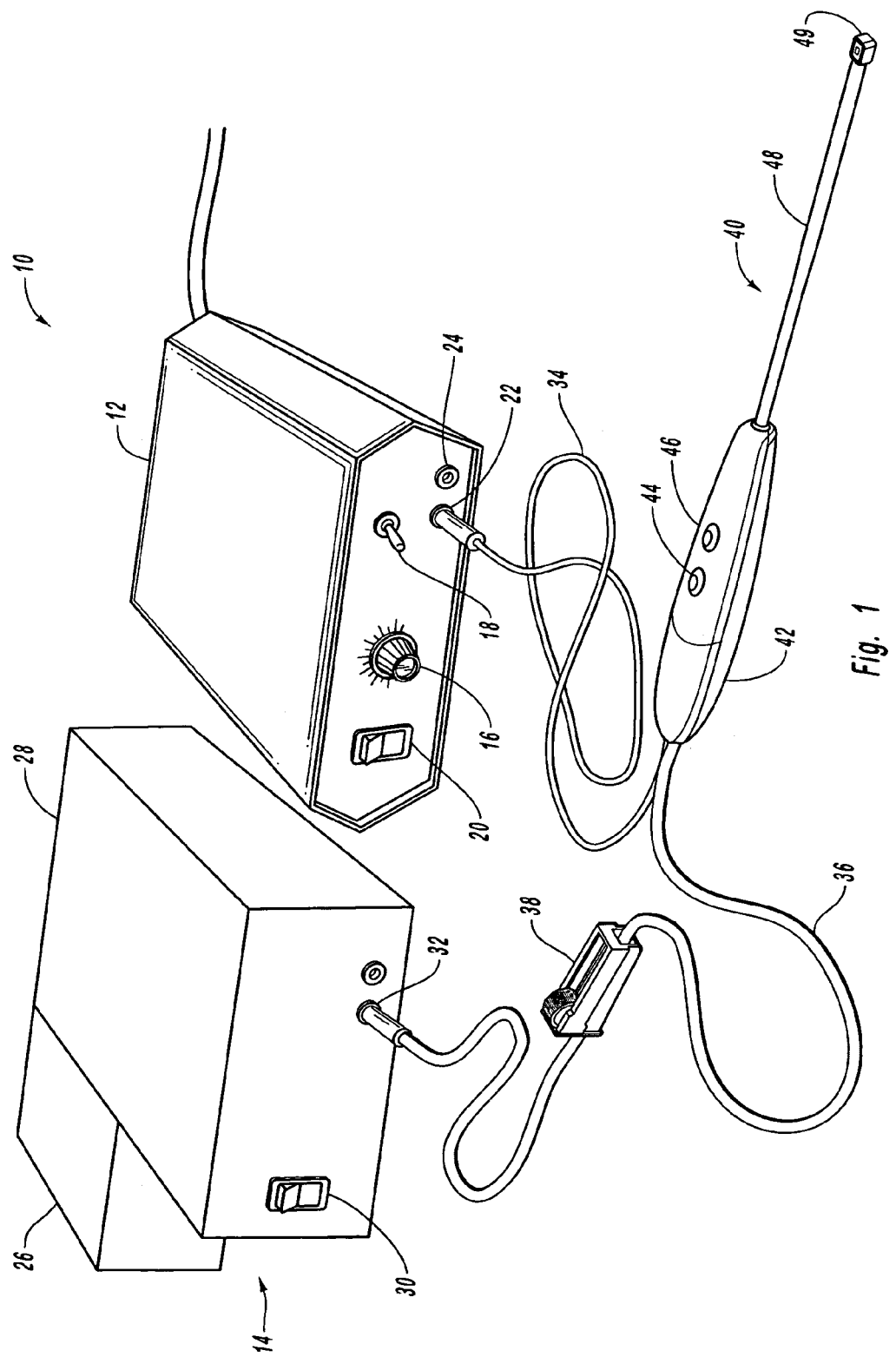
FIG. 1 is a perspective view of an electrosurgical instrument including a radio frequency generator, an aspirator, and an electrosurgical probe according to an embodiment of the invention.

FIG. 1 shows an exemplary electrosurgical system according to one embodiment of the invention. The electrosurgical system 10 includes an electrosurgical probe 40 that is electrically coupled to an electrosurgical generator 12 and an aspirator 14.

Electrosurgical generator 12 is configured to generate radio frequency ("RF") wave forms. Generator 12 can generate power useful for ablating tissue and/or coagulating tissue. In one embodiment, generator 12 includes standard components, such as dial 16 for controlling the frequency and/or amplitude of the RF energy, a switch 18 for changing the type of waveform generated (e.g. between cut and coag), a switch 20 for turning the generator on and off, and an electrical port 22 for connecting the electrosurgical instrument 10. Generator 12 also includes port 24 for connecting an electrical ground or a return electrode. It will be appreciated that generator 12 can be designed for use with bipolar electrosurgical instruments instead of, or in addition to, monopolar devices.

Aspirator 14 includes a pump 26, a reservoir 28, an on/off switch 30, and an aspirator port 32. Pump 26 provides negative pressure for aspirating fluids, gasses, and debris through electrosurgical instrument 10. Aspirated fluids and debris can be temporarily stored in reservoir 28. In another embodiment, electrosurgical instrument 10 is connected to wall suction. When using wall suction, canisters or other reservoirs are placed in the suction line to collect aspirated tissue and fluids. Those skilled in the art will recognize that many different configurations of generator 12 and aspirator 14 can be used in the present invention.

Electrosurgical instrument 40 is depicted as an elongate probe and includes a power cord 34 for electrically connecting instrument 40 to generator 12 through electrical port 22. Extension tubing 36 provides a fluid connection between instrument 40 and aspirator 14. A flow control device 38 allows a practitioner to vary the rate of aspiration through instrument 40.

The electrosurgical instrument 40 includes a proximal end portion 42 and a distal end portion 48. In one embodiment, proximal end portion 42 can provide a handle for instrument 40. Distal end portion 48 of probe 40 includes an electrode head 49, which includes a plurality of electrodes.

Instrument 40 can be used for selectively ablating or coagulating tissue in a patient. Buttons 44 and 46 on the proximal end portion 42 can be used to switch instrument 40 between a first operational mode for ablating tissue and a second operational mode for coagulating tissue and are examples of a user operable input component.

Figure 2:
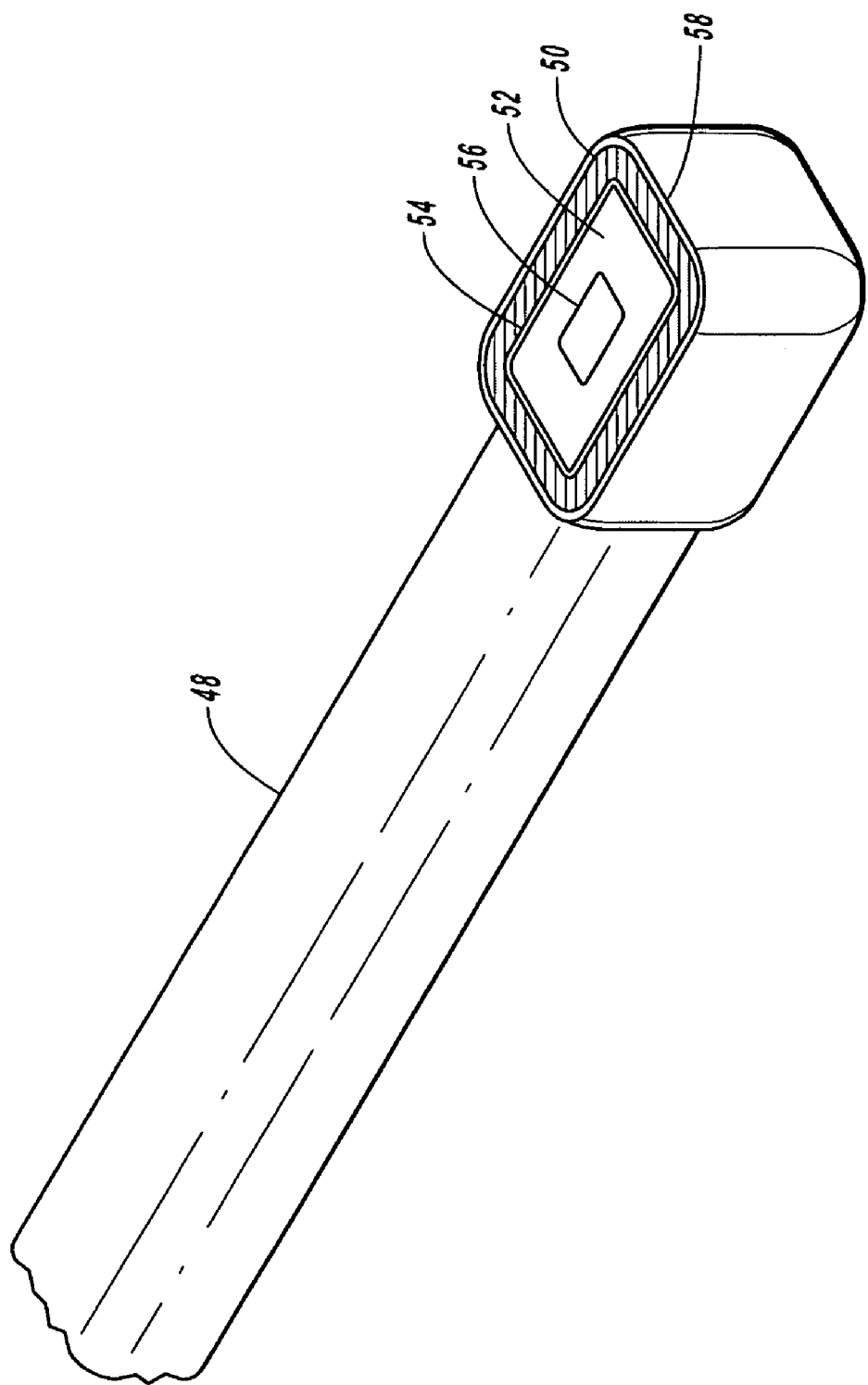
FIG. 2 is a perspective view of an exemplary embodiment of a distal portion of the probe of the electrosurgical instrument of FIG. 1.

Instrument 40 includes at least two active electrodes that are physically and electrically configured to provide a larger active surface area when instrument 40 is in the coagulation mode compared to the active surface area when instrument 40 is in the coagulation mode. FIG. 2 illustrates an exemplary embodiment of an electrode configuration that provides a greater active surface area in a coagulation mode compared to an ablation mode. As shown in FIG. 2, instrument 40 includes a first electrode 50 and a coagulation electrode 52 on distal end portion 48. First electrode 50 and coagulation electrode 52 are conductive elements such as a metal or other suitable material for conducting a current. First electrode 50 and second electrode 52 are electrically isolated from one another by insulating material 54. In this embodiment, electrode 50 and 52 are concentric with one another. However, the invention includes electrode configurations where the first electrode and the coagulation electrode are not concentric, as described more fully below with respect to FIGS. 6A-6D. An outer insulative material 58 provides a protective covering on the distal end portion 48 of instrument 40, while leaving electrodes 50 and 52 exposed.

An aspiration lumen 56 can be positioned within electrode 50. Aspiration lumen 56 can be used with aspirator 14 (FIG. 1) to withdraw fluids and debris from the surgical site during ablation. In a preferred embodiment, aspiration lumen is located within second electrode 52 to provide some distance between first electrode 50 and aspiration lumen 56. This distance between first electrode 50 and aspiration lumen 56 can be beneficial since aspirating fluids tends to have a cooling effect on adjacent surroundings and cooling can be undesirable for achieving a plasma in the ablation mode. However, those skilled in the art will recognize that an aspiration lumen 56 is not required to carry out the invention and that the aspiration lumen 56 can be located in various places on instrument 40, if desired.

First electrode 50 is configured to provide ablation when instrument 40 is in the ablation mode. Electrodes that are configured for ablation have a surface area that can create a plasma in an aqueous medium when power from power source 12 is delivered to the electrode. The particular configuration of the first electrode that allows ablation to be achieved will depend on the power for which the instrument 40 is designed to operate. In one embodiment, instrument 40 is designed to operate within a range from about 150 W to about 500 W, more preferably about 200 W to about 400 W. For a power rating of about 400 W, the surface area can be in a range from about 3 $mm^2$ to about 30 $mm^2$, more preferably about 5 $mm^2$ to about 25 $mm^2$, and most preferably about 7 $mm^2$ to about 20 $mm^2$.

Coagulation electrode 52 is configured to perform coagulation in a tissue, either alone or in combination with one or more auxiliary electrodes (e.g., electrode 50). Electrodes that are configured for coagulation have an active surface area that does not create a plasma in an aqueous medium when power from power source 12 is delivered to the electrode, but have sufficiently small surface area such that power from power source 12 will generate sufficient heat to cause coagulation in a tissue. For example, for a power rating of about 400 W, the active surface area during coagulation can be in a range from 10 $mm^2$ to about 50 $mm^2$. The coagulation electrode 52 is greater in size than the first electrode, which allows coagulation to occur instead of ablation. In one embodiment, the coagulation electrode that is active during coagulation is at least 10% larger in surface area than the surface area of the first electrode, alternatively at least 15% larger, 25% larger, or even 50% larger in surface area. Those skilled in the art are readily familiar with selecting suitable power levels and electrode surface areas to achieve coagulation in the tissue of a patient. The coagulation electrode 52 also has a surface area that is smaller than the return electrode. In one embodiment the surface area of the return electrode is at least 10% smaller than the surface area of the return electrode, alternatively at least 15% smaller, 25% smaller, or even 50% smaller in surface area.

The surface area required to configure an electrode for ablation or coagulation will depend on the power to be delivered to the device. It is customary in the art to provide power generators that allow a practitioner to adjust the power. For purposes of this invention, the determination as to whether the electrode 50 is configured for ablation and electrode 52 is configured for coagulation is made in reference to a single power setting (i.e., first electrode 50 ablates at a design power and coagulation electrode alone or in combination coagulates at the same design power). However, it will be understood that in use a practitioner may chose to select different power settings for the ablation mode and coagulation mode, so long as the power settings provide ablation in an ablation mode and coagulation in a coagulation mode.

Electrodes 50 and 52 are configured to allow a user to selectively operate instrument 40 in a coagulation mode or an ablation mode. The user selects between the two operational modes by actuating a user operable input component (e.g. a switch). The user operable input component can be any type of mechanical or electrical input device that causes a change in the amount of active surface area on instrument 40 so as to cause electrode 50 and/or electrode 52 to operate under coagulation conditions or alternatively to operate under ablation conditions.

In one embodiment, the user input component can be a mechanical switch. Examples of mechanical switches include push button switches, lever actuated switches, foot pedal switches, etc. Those skilled in the art will recognize that there are many different types of switches that can be employed in the present invention as a user operable input device.

Figure 3A:
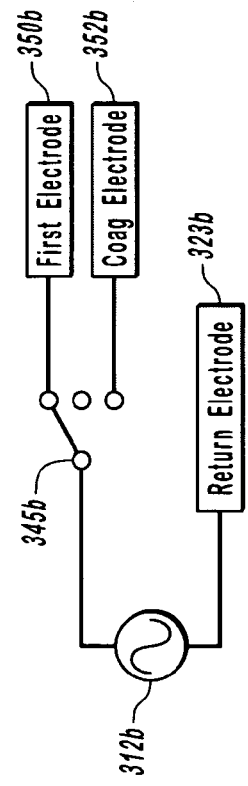
FIG. 3A is an exemplary circuit diagram of an electrosurgical instrument according to the present invention.
Figure 3B:
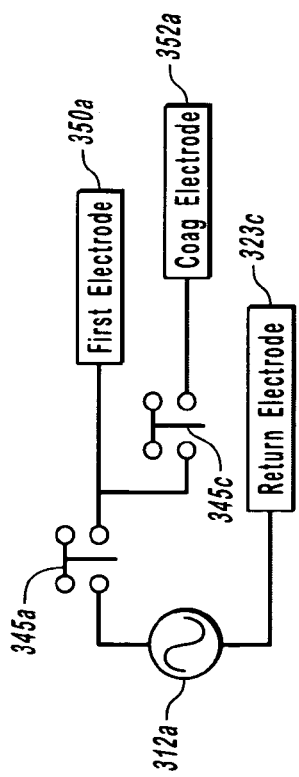
FIG. 3B is an alternative circuit diagram of an electrosurgical instrument according to the present invention.

When actuated, the user operable input component causes power to be delivered either to one or both of first electrode 50 and coagulation electrode 52. FIGS. 3A and 3B are circuit diagrams illustrating exemplary electrical configurations that allow a user to selectively switch between a coagulation mode and an ablation mode by changing the active surface area to achieve the two different modes. FIG. 3A illustrates an electrical configuration where first electrode 350*a* performs ablation when instrument 40 is in an ablation mode and coagulation electrode 352*a*, together with first electrode 350*a*, performs coagulation when instrument 40 is in a coagulation mode.

In FIG. 3A, a power source 312*a* is electrically coupled to an on/off switch 345*a* and a return electrode 323*c*. On/off switch 345*a* is electrically coupled to first electrode 350*a* and a selector switch 345*c*. Selector switch 345*c* is electrically coupled to coagulation electrode 352*a*. FIG. 3A illustrates instrument 10 in an off position. To achieve the ablation mode, a user actuates on/off switch 345*a*, which delivers current from RF generator 312*a* to first electrode 350*a*. The circuit is completed by current traveling through tissue or fluids within a patient to return electrode 323*c*. With on/off switch 345*a* actuated and selector switch 345*c* deactivated, coagulation electrode 352 is off (i.e., inactive). Thus, the active surface area is provided by first electrode 350*a*. First electrode 350*a* has a surface area suitable for carrying out ablation when activated by RF generator 312*a* with selector switch 345*c* in the off position.

To achieve the coagulation operational mode, the user actuates selector switch 345*c*, which then delivers a portion of the current to coagulation electrode 352*a*, thereby activating the surface of coagulation electrode 352*a*. The circuit for both the first electrode 350*a* and the coagulation electrode 352*a* are completed through fluids or tissue electrically coupled to return electrode 323*c*. In the coagulation mode, current is shared between first electrode 350*a* and coagulation electrode 352*a*, thereby reducing the current to first electrode 350*a* (compared to the current delivered to first electrode 350*a* in the ablation mode). The active surface area in the coagulation mode is the sum of the active area on the first electrode 350*a* and the coagulation electrode 352*a*, which is greater than the active surface area in the ablation mode (i.e., just the first electrode 350*a*). The increased surface area results in a sufficiently low current density to avoid generating a plasma, but sufficiently high current density to cause coagulation.

FIG. 3B is a circuit diagram of a probe according to the invention that has a pole switch 345*b* that allows current to be selectively delivered to first electrode 350*b* or coagulation electrode 352*b*. RF generator 312*b* is electrically coupled to pole switch 345*b* and return electrode 323*b*. Pole switch 345*b* can be switch by a user between three positions which correspond to ablation mode, coagulation mode, and off. Pole switch 345*b* is shown positioned in the ablation mode. In this configuration, current from RF generator is delivered to only first electrode 350*b*. Actuation by a user can position pole switch 345*b* in a middle position, in which case the probe is in an off position. Further movement of pole switch 345*b* to the bottom position activates coagulation electrode 352*b*, but not first electrode 350*b*. Coagulation electrode 352 has a greater active surface area than ablation electrode 350*b*. Consequently, the current density on coagulation electrode 352 is less compared to the current density of first electrode 350*b* with pole switch 345*b* positioned in the ablation mode. The lower current density in the coagulation mode results in coagulation rather than ablation, even if the power output of RF generator 312*b* is the same, greater, or less than the power output with pole switch 345*b* positioned in the ablation mode.

In the embodiment shown in FIG. 3B the coagulation electrode 352*b* will typically have a larger surface area than the ablation electrode 352*a*. However, in the embodiment shown in FIG. 3A, the surface area of the coagulation electrode 352*a* can be the same, larger, or smaller than the first electrode 350*a*, so long as the total active surface area during coagulation is larger than the active surface area during ablation.

Figure 4A:
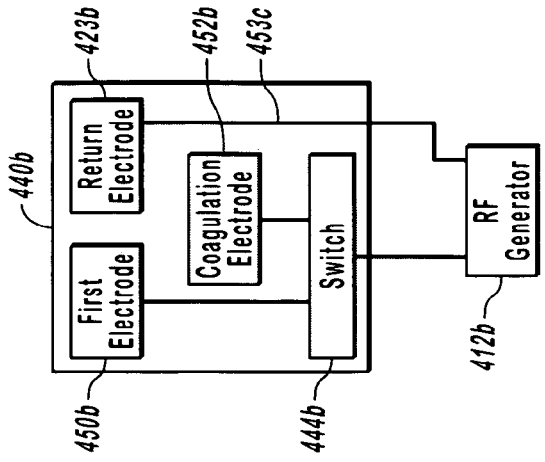
FIG. 4A is a schematic diagram of the electrode configuration of an exemplary monopolar instrument according to an embodiment of the present invention.
Figure 4B:
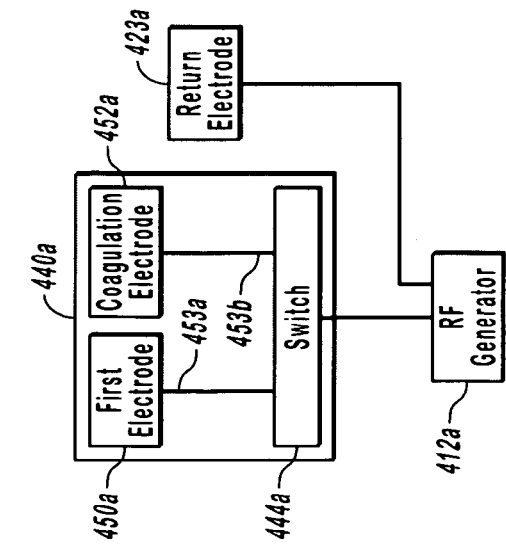
FIG. 4B is a schematic diagram of the electrode configuration of a bipolar instrument according to another embodiment of the present invention.

FIGS. 4A and 4B are schematic diagrams showing the incorporation of a switch and electrodes into a probe or instrument. FIGS. 4A and 4B illustrate monopolar and bi-polar electrode configurations, respectively. In FIG. 4A, a probe 440*a* includes a first electrode 450*a*, a coagulation electrode 452*a*, and a switch 444*a*, which is an example of a user operable input component. Probe 440*a* is electrically coupled to RF generator 412*a*. A return electrode 423*a* is electrically coupled to RF generator 412*a*. In this embodiment, return electrode 423*a* is not incorporated into probe 440*a*. Return electrode 423 is therefore placed on the body of a patient to provide a completed electrical circuit. The monopolar configuration illustrated in FIG. 4A includes two leads 453*a*, 453*b* that electrically couple switch 444*a* with first electrode 450*a* and coagulation electrode 452*a*. This monopolar configuration can be advantageous because it eliminates the complexity involved with incorporating additional electrodes into the probe, which can be very small.

FIG. 4B illustrates a bipolar configuration where probe 440*b* includes a first electrode 450*b*, a coagulation electrode 452*b*, and a return electrode 423*b* electrically coupled to RF generator 412*b*. Return electrode 423*b* is incorporated into probe 440*b* and electrically coupled to switch 444*b* through a lead 453*c*. Switch 444*b* is an example of a user operable input component. Placing return electrode 423 on probe 440*b* can be advantageous because it reduces the amount of current that travels through the patient during operation and it eliminates the need to have a separate cord properly attached to the patient.

While FIGS. 4A and 4B illustrate monopolar and bipolar configurations, the invention is not limited to a monopolar or bipolar configuration and additional separate electrodes can be placed on the probe, provided there is sufficient surface area.

While switches 444*a* and 444*b* have been shown as incorporated into probe 440*a* and 440*b*, respectively, those skilled in the art will recognize that the switch can be external to the probe. For example, the switch can be incorporated into a foot pedal that is electrically coupled to the RF generator and probe 440.

Figure 5:
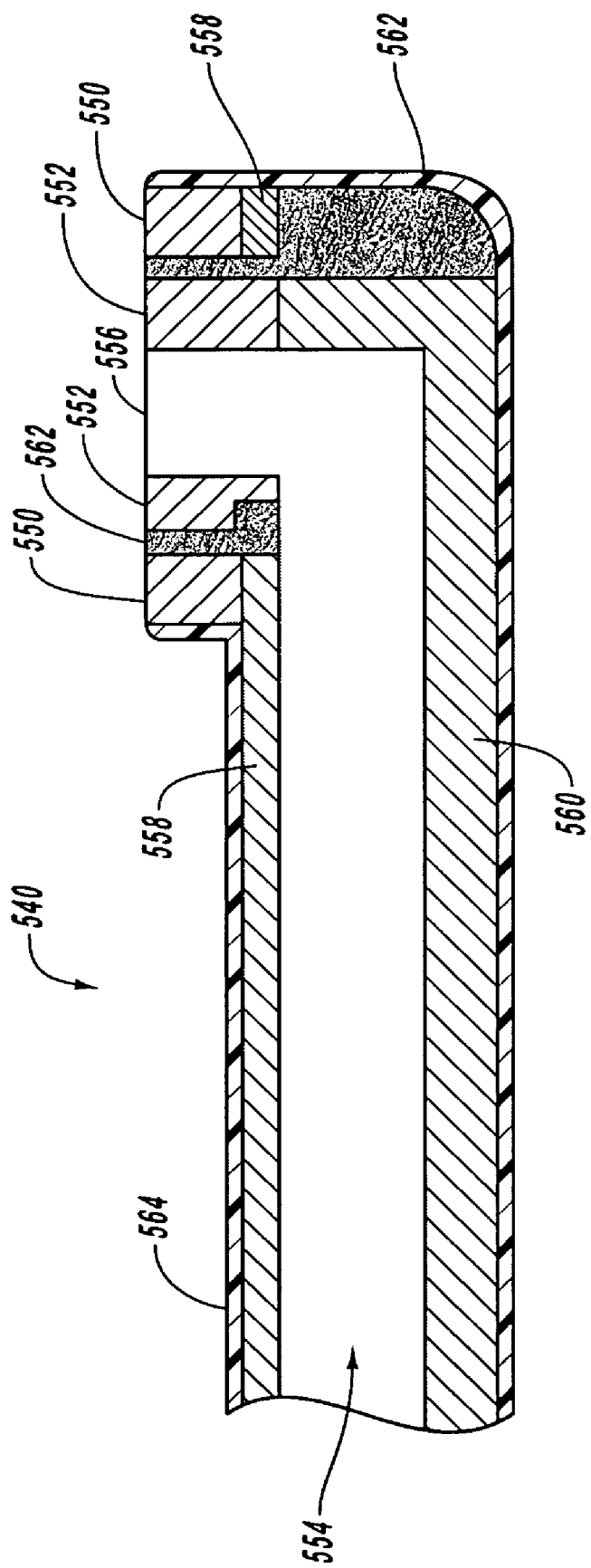
FIG. 5 is a cross sectional view of an exemplary monopolar electrosurgical instrument according to an embodiment of the invention.

The present invention encompasses devices having a wide variety of configurations. Typically the instrument or probe will have a hollow tube with electrical leads incorporated into the tubing and leading to a distal end. FIG. 5 illustrates a cross section of an exemplary monopolar probe 540 according to one embodiment of the invention. Probe 540 is a cross section of an electrode head substantially similar to that shown in FIG. 1. Probe 540 forms an elongate tube having an aspiration lumen 554 that leads to an aspiration opening 556 at a distal end of probe 540. Probe 550 includes a first electrical lead 558 that is electrically coupled to first electrode 550. First electrode 550 may be configured to carry out ablation when activated. Second electrical lead 560 is electrically coupled to second electrode 552. Second electrode 552 may be configured to cause coagulation in a coagulation mode of the device. First electrode 550 and second electrode 552 are electrically isolated by insulative material 562, 564. Similarly, leads 558 and 560 are electrically isolated from one another. Those skilled in the art are familiar with configuring electrodes and insulators to provide electrical isolation while allowing current from the RF generator to power the electrode.

The particular configuration of the first electrode and second electrode can be varied. For example the first electrode and second electrode can be concentric rectangles as shown in FIG. 1. FIGS. 6A-6D illustrate alternative configurations of electrodes. FIG. 6A illustrates an electrode head 649*a* with circular concentric electrodes. Electrode head 649*a* includes a first electrode 650a, a second electrode 652a and an insulative material 654a electrically isolating the two. An optional aspiration lumen 556a is positioned within second electrode 652a. Although FIG. 6A shows the first electrode 650a outside of the second (e.g., coagulation) electrode 652a, those skilled in the art will recognize that the concentric electrodes can be reversed such that the coagulation electrode 652a is outside of the first electrode 650a.

Figure 6B:
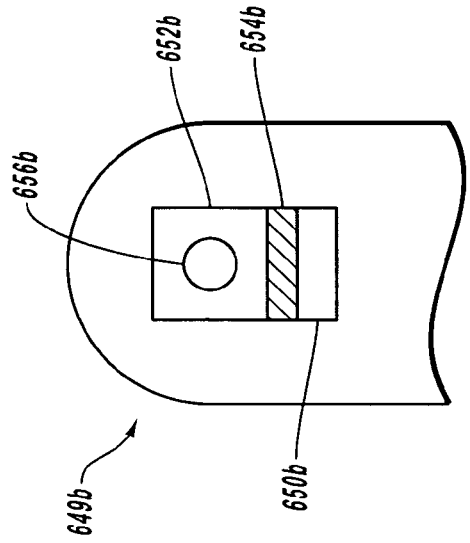
FIGS. 6A-6D illustrate various embodiments of electrode configurations according to the present invention.

FIG. 6B illustrates an electrode configuration that is not concentric. In this embodiment, an electrode head 649b includes a first electrode 650b that is configured for ablation and a second electrode 652b that is configured to coagulate (alone or in combination with first electrode 650b). Insulative material 654b electrically isolates first electrode 650b from second electrode 652b. An optional aspiration lumen 656b is positioned within second electrode 652b.

Figure 6D:
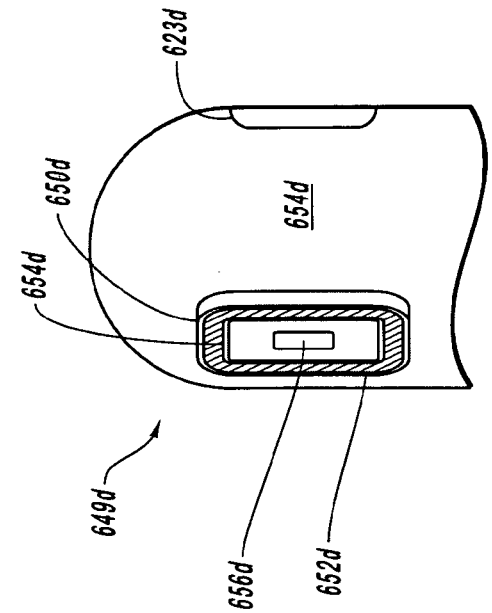
Figure 6A:
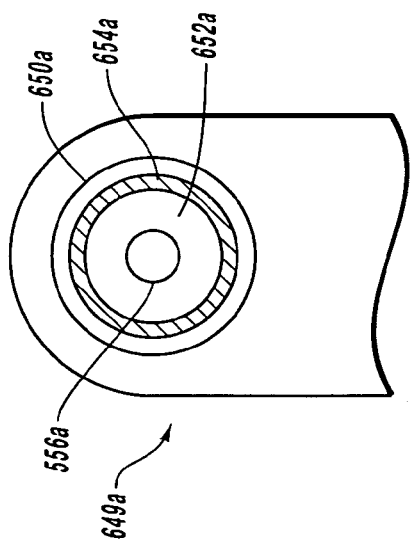
Figure 6C:
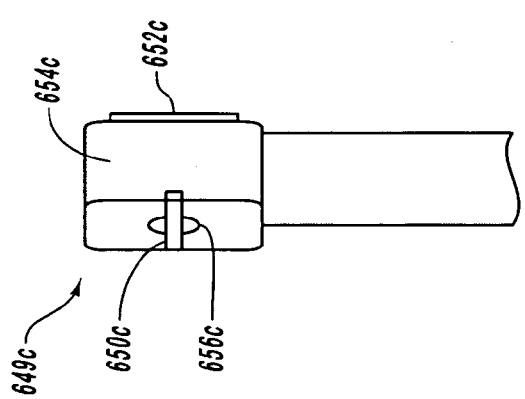

FIG. 6C illustrates an alternative embodiment having a first electrode 650c positioned over an aspiration lumen 656c. A coagulation electrode 652c is positioned on an opposite side of electrode head 649c from first electrode 650c. Electrode head 649c can be formed from an insulating material 654c to electrically isolate first electrode 650c and coagulation electrode 652c.

FIG. 6D illustrates a bi-polar electrode head 649d. Bi-polar electrode head 649d includes a first electrode 650d that is concentric to second (e.g., coagulation) electrode 652d and aspiration lumen 656d. Electrode head 649d also include a return electrode 623d. Return electrode 623d, first electrode 650d, and coagulation electrode 652d are electrically isolated using an insulative material 654d. Return electrode 623d has a sufficiently large surface area that very little heat is generated from current passing through it, such that return electrode 623a does not cause coagulation.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An electrosurgical instrument or system for selectively ablating or coagulating tissue at a surgical site during a surgical procedure, the electrosurgical instrument or system being switchable between an ablation mode and a coagulation mode, the electrosurgical instrument or system comprising:
   an elongate probe having a proximal end portion and a distal end portion;
   a first electrode positioned at the distal end portion of the elongate probe, the first electrode having a first surface area so as to generate a first current density sufficient to ablate tissue when a first amount of power is delivered to the first electrode during operation in an ablation mode;
   a coagulation electrode positioned at the distal end portion and electrically isolated from the first electrode, the coagulation electrode having a second surface area that is at least 10% greater than the first surface area so as to generate a second current density that is less than the first current density so as to coagulate tissue when a second amount of power greater than the first amount of power is delivered to the coagulation electrode during operation in a coagulation mode; and
   a user operable switch electrically coupled to the first electrode and to the coagulation electrode for selectively delivering power from a power generator to one or both of the first electrode or coagulation electrode, the user operable switch providing user selectable switching between the ablation mode and the coagulation mode, wherein:
   when the electrosurgical instrument or system operates in the ablation mode, the switch selectively causes the first amount of power to be delivered only to the first electrode and not to the coagulation electrode so as to generate the first current density at the first electrode sufficient to ablate tissue, and
   when the electrosurgical instrument or system operates in the coagulation mode, the switch selectively causes the second amount of power to be delivered to at least the coagulation electrode so as to generate the second current density at the coagulation electrode and optionally also at the first electrode sufficient to coagulate tissue.

2. An electrosurgical instrument or system as in claim 1, wherein, in the coagulation mode, the switch causes a first portion of the second amount of power to be delivered to the first electrode and a second portion of the second amount of power to be delivered to the coagulation electrode, thereby configuring the first electrode for coagulation instead of ablation as a result of increased total electrode surface area.

3. An electrosurgical instrument or system as in claim 1, wherein the first electrode and the coagulation electrode comprise concentric surfaces separated by an insulating material.

4. An electrosurgical instrument or system as in claim 3, further comprising an aspiration lumen in the distal portion, the aspiration lumen having an opening surrounded by the coagulation electrode.

5. An electrosurgical instrument or system as in claim 1, wherein at least one of the first electrode and the coagulation electrode comprises a plurality of distinct surface areas each separated by an insulating material.

6. An electrosurgical instrument or system as in claim 1, wherein the total electrode surface area that is activated when operating in the coagulation mode is at least 15% larger than when operating in the ablation mode.

7. An electrosurgical instrument or system as in claim 1, wherein the second electrode surface area that is activated when operating in the coagulation mode is at least 25% larger than when operating in the ablation mode.

8. An electrosurgical instrument or system as in claim 1, wherein the elongate probe is monopolar.

9. An electrosurgical instrument or system as in claim 8, further comprising a return electrode that is sized and configured to be attached to an external part of the body of a patient.

10. An electrosurgical instrument or system as in claim 1, wherein the elongate probe is bipolar, the elongate probe comprising a return electrode positioned on the distal end portion thereof.

11. An electrosurgical instrument or system as in claim 1, further comprising an RF generator, wherein the user operable switch comprises a foot pedal electrically coupled to the RF generator.

12. An electrosurgical instrument or system as in claim 1, wherein the user operable switch is incorporated into the proximal end portion of the elongate probe.

13. A method for operating an electrosurgical instrument at a surgical site, comprising:
   (i) providing an electrosurgical instrument or system as in claim 1;
   (ii) coupling the electrosurgical instrument to an RF generator, the RF generator providing a total quantity of power to the electrosurgical instrument;
   (iii) selecting the ablation mode for the electrosurgical instrument using the user operable switch and operating the electrosurgical instrument in the ablation mode, wherein in the ablation mode, a part of the total quantity of power is delivered only to the first electrode and not to the coagulation electrode so as to cause ablation of tissue at the surgical site; and (iv) selecting the coagulation mode for the electrosurgical instrument using the user operable switch and operating the electrosurgical instrument in the coagulation mode, wherein in the coagulation mode, a greater part of the total quantity of power is delivered to the coagulation electrode and optionally also to the first electrode while causing coagulation of tissue at the surgical site, and wherein when operating in the coagulation mode a lower electrode current density is generated while delivering the greater part of the total quantity of power as compared to when operating in the ablation mode.

14. A method as in claim 13, wherein operating the electrosurgical instrument in the coagulation mode comprises delivering a portion of the total quantity of power from the RF generator to the first electrode and delivering a second portion of the total quantity of power to the coagulation electrode to further increase total electrode surface area.

15. A method as in claim 13, wherein the total quantity of power of the RF generator is in a range from 150 W to 600 W.

16. A method as in claim 13, wherein the total quantity of power of the RF generator is in a range from about 200 W to about 400 W.

17. A method as in claim 13, wherein step (iii) is performed prior to step (iv).

18. A method as in claim 13, wherein step (iv) is performed prior to step (iii).

19. A method as in claim 13, further comprising aspirating fluids through a lumen in the elongate probe while operating the electrosurgical instrument in the ablation mode.

20. An electrosurgical instrument for selectively ablating or coagulating tissue at a surgical site during a surgical procedure, comprising:
an elongate probe having a proximal end portion and a distal end portion;
a first electrode positioned at the distal end portion of the elongate probe, the first electrode having a first surface area so as to generate a first current density sufficient to ablate tissue when a first amount of power is delivered to the first electrode during operation in an ablation mode;
a coagulation electrode positioned at the distal end portion and electrically isolated from the first electrode, the coagulation electrode and the first electrode providing a combined surface area greater than the first surface area so as to generate a second current density that is less than the first current density when a second amount of power that is the same or greater than the first amount of power is simultaneously delivered to both the coagulation electrode and the first electrode in order for the coagulation electrode and first electrode to coagulate tissue during operation in a coagulation mode; and
a user operable switch electrically coupled to the first electrode and to the coagulation electrode for selectively delivering power from a power generator to only the first electrode during operation of the electrosurgical instrument in the ablation mode and power to both the coagulation electrode and the first electrode during operation of the electrosurgical instrument in the coagulation mode, wherein
when the electrosurgical instrument operates in the ablation mode, the switch selectively causes the first amount of power to be delivered only to the first electrode and not the coagulation electrode so as to generate the first current density at the first electrode sufficient to ablate tissue, and
when the electrosurgical instrument operates in the coagulation mode, the switch selectively causes the second amount of power to be simultaneously delivered to both the coagulation electrode and the first electrode so as to generate the second current density at the coagulation electrode and the first electrode that is less than the first current density and that is sufficient to coagulate tissue.

21. An electrosurgical instrument as in claim 20, wherein the coagulation electrode has a larger surface area than the first surface area of the first electrode.

22. An electrosurgical instrument as in claim 20, wherein the coagulation electrode has a smaller surface area than the first surface area of the first electrode.

23. An electrosurgical instrument as in claim 20, wherein the coagulation electrode has a surface area equal to the first surface area of the first electrode.

24. A method for operating an electrosurgical instrument at a surgical site, comprising: (i) providing an electrosurgical instrument as in claim 20; (ii) coupling the electrosurgical instrument to an RF generator, the RF generator providing a total quantity of power to the electrosurgical instrument; (iii) selecting the ablation mode for the electrosurgical instrument using the user operable switch and operating the electrosurgical instrument in the ablation mode, wherein in the ablation mode, the total quantity of power is delivered only to the first electrode and not to the coagulation electrode so as to cause ablation of tissue at the surgical site; and (iv) selecting the coagulation mode for the electrosurgical instrument using the user operable switch and operating the electrosurgical instrument in the coagulation mode, wherein in the coagulation mode, a same or greater total quantity of power is delivered to both the coagulation electrode and the first electrode while causing coagulation of tissue at the surgical site, and wherein when operating in the coagulation mode a lower electrode current density is generated at the coagulation electrode and the first electrode while delivering the same or greater total quantity of power as compared to when operating in the ablation mode.

25. An electrosurgical instrument for selectively ablating or coagulating tissue at a surgical site, the electrosurgical instrument being switchable between an ablation mode and a coagulation mode, the electrosurgical instrument comprising:
an elongate probe having a proximal end portion and a distal end portion;
a dedicated ablation electrode positioned at the distal end portion of the elongate probe, the dedicated ablation electrode having a first surface area so as to generate a first current density sufficient to ablate tissue when a first amount of power is delivered to the dedicated ablation electrode during operation in an ablation mode;
a dedicated coagulation electrode positioned at the distal end portion and electrically isolated from the dedicated ablation electrode, the dedicated coagulation electrode having a second surface area that is at least 10% greater than the first surface area of the ablation electrode so as to generate a second current density sufficient to only coagulate tissue when a second amount of power greater than the first amount of power is delivered to the dedicated coagulation electrode; and
a user operable switch electrically coupled to the ablation electrode and to the coagulation electrode for selectively delivering power from a power generator to the ablation or coagulation electrode, the user operable switch providing user selectable switching between the ablation electrode and the coagulation electrode, wherein, when the electrosurgical instrument operates in the ablation mode, the switch selectively causes the first amount of power to be delivered only to the dedicated ablation electrode and not to the dedicated coagulation electrode so as to generate the first current density at the dedicated ablation electrode sufficient to ablate tissue, and when the electrosurgical instrument operates in the coagulation mode, the switch selectively causes the second amount of power to be delivered only to the dedicated coagulation electrode and not to the dedicated ablation electrode so as to generate the second current density at the dedicated coagulation electrode sufficient to coagulate tissue.

26. An electrosurgical instrument as in claim 25, wherein the second surface area is at least 15% larger than the first surface area.

27. An electrosurgical instrument as in claim 25, wherein the second surface area is at least 25% larger than the first surface area.

28. A method for operating an electrosurgical instrument at a surgical site, comprising: (i) providing an electrosurgical instrument as in claim 25; (ii) coupling the electrosurgical instrument to an RF generator, the RF generator providing a total quantity of power to the electrosurgical instrument; (iii) selecting the ablation mode for the electrosurgical instrument using the user operable switch and operating the electrosurgical instrument in the ablation mode, wherein in the ablation mode, the total quantity of power is delivered only to the first electrode and not to the coagulation electrode so as to cause ablation of tissue at the surgical site; and (iv) selecting the coagulation mode for the electrosurgical instrument using the user operable switch and operating the electrosurgical instrument in the coagulation mode, wherein in the coagulation mode, a greater total quantity of power is delivered to the coagulation electrode while causing coagulation of tissue at the surgical site, and wherein when operating in the coagulation mode a lower electrode current density is generated at the coagulation electrode while delivering the greater total quantity of power as compared to when operating in the ablation mode.

* * * * *

UNITED STATES PATENT AND TRADEMARK OFFICE
CERTIFICATE OF CORRECTION

PATENT NO. : 8,361,065 B2  
APPLICATION NO. : 12/171150  
DATED : January 29, 2013  
INVENTOR(S) : West, Jr.

Page 1 of 1

It is certified that error appears in the above-identified patent and that said Letters Patent is hereby corrected as shown below:

In the Specifications

Column 1  
Line 23, change "of few" to --of a few--

Column 3  
Line 7, change "power that" to --power than--  
Line 38, change "between an" to --between a--

Column 5  
Line 27, change "coagulation" to --ablation--

Column 6  
Line 40, change "chose" to --choose--

Column 7  
Line 44, change "switch" to --switched--  
Line 46, change "generator" to --generator 312b--

Column 8  
Line 11, change "423" to --423a--  
Line 25, change "423" to --423b--  
Line 39, change "generator" to --generator 412--  
Line 50, change "Probe 550" to --Probe 540--

Column 9  
Line 27, change "include" to --includes--

Signed and Sealed this  
First Day of October, 2013

Teresa Stanek Rea  
*Deputy Director of the United States Patent and Trademark Office*